(12) United States Patent
Krishnan

(10) Patent No.: US 9,958,374 B2
(45) Date of Patent: May 1, 2018

(54) METHOD AND APPARATUS FOR MEASURING CHARGE AND SIZE OF SINGLE OBJECTS IN A FLUID

(71) Applicant: UNIVERSITAT ZURICH, Zurich (CH)

(72) Inventor: Madhavi Krishnan, Zurich (CH)

(73) Assignee: UNIVERSITAT ZURICH, Zurich (CH)

( * ) Notice: Subject to any disclaimer, the term of this patent is extended or adjusted under 35 U.S.C. 154(b) by 536 days.

(21) Appl. No.: 14/390,034

(22) PCT Filed: Mar. 28, 2013

(86) PCT No.: PCT/EP2013/000942
§ 371 (c)(1),
(2) Date: Oct. 2, 2014

(87) PCT Pub. No.: WO2013/149715
PCT Pub. Date: Oct. 10, 2013

(65) Prior Publication Data
US 2015/0081228 A1    Mar. 19, 2015

(30) Foreign Application Priority Data
Apr. 3, 2012 (EP) .................................. 12002407

(51) Int. Cl.
*G01N 15/00* (2006.01)
*G01N 15/02* (2006.01)
(Continued)

(52) U.S. Cl.
CPC ......... *G01N 15/10* (2013.01); *G01N 15/0211* (2013.01); *G01N 15/0266* (2013.01);
(Continued)

(58) Field of Classification Search
None
See application file for complete search history.

(56) References Cited

U.S. PATENT DOCUMENTS

| 7,755,765 B2 * | 7/2010 | Post | .................. | G01C 21/16 |
| | | | | 356/450 |
| 2011/0036719 A1 * | 2/2011 | Neyts | ................. | G01N 15/1031 |
| | | | | 204/549 |

FOREIGN PATENT DOCUMENTS

WO    WO2009/127688    10/2009

OTHER PUBLICATIONS

Madhavi Krishnan et al: "Geometry-induced electrostatic trapping of nanometric objects in a fluid", Nature, vol. 467, No. 7316, Oct. 7, 2010, pp. 692-695.

* cited by examiner

*Primary Examiner* — An Do
*Assistant Examiner* — Renee I Wilson
(74) *Attorney, Agent, or Firm* — JMB Davis Ben-David

(57) ABSTRACT

In a method for determining charge and/or size of an object (15) suspended in a fluid, the object (15) is introduced, together with the fluid, into an electrostatic trap (1) defining an electrostatic confining potential. The thermal motion of the object (15) in the fluid is observed under influence of the confining potential, and charge and/or size are determined from the observed thermal motion. In particular, the viscous drag on the object yields a measure of its size, while the stiffness of its confinement can be compared with a potential model to reveal the total charge it carries. Also disclosed are an apparatus and software for carrying out the method.

15 Claims, 7 Drawing Sheets

(51) Int. Cl.
*G01N 25/00* (2006.01)
*G01N 15/14* (2006.01)
*B82Y 35/00* (2011.01)
*G01N 15/10* (2006.01)

(52) U.S. Cl.
CPC ..... *G01N 15/1031* (2013.01); *G01N 15/1463* (2013.01); *G01N 25/00* (2013.01); *B82Y 35/00* (2013.01); *G01N 2015/0038* (2013.01); *G01N 2015/1075* (2013.01); *G01N 2015/1087* (2013.01)

US 9,958,374 B2

METHOD AND APPARATUS FOR MEASURING CHARGE AND SIZE OF SINGLE OBJECTS IN A FLUID

CROSS-REFERENCE TO RELATED APPLICATIONS

This is the U.S. National Stage of International Application No. PCT/EP2013/000942, filed Mar. 28, 2013, which was published in English under PCT Article 21(2), and which in turn claims the benefit of EP Patent Application No. 12002407.0, filed Apr. 3, 2012.

TECHNICAL FIELD

The present invention relates to a method for determining the electric charge and/or the size of an object suspended in a fluid. The invention further relates to a corresponding apparatus and to software for carrying out the method.

PRIOR ART

Colloidal suspensions are of interest in a wide range of industrial and consumer products, in research and medical diagnostics. From paints and cement to vaccines and proteins, sample characterization plays a vital role in quality control of the final suspension. Particle size and charge are two major properties of interest in colloidal suspensions.

Currently, the most important techniques for measuring size and charge of nanoscale objects in suspensions are based on light scattering. As the intensity of light scattered by a small object scales as the sixth power of its size, such techniques are inherently biased to larger entities, e.g., to aggregates in the sample. Other known methods for size and/or charge determination such as capillary electrophoresis, field-flow fractionation and analytical ultracentrifugation, draw on the collective migration of species in response to external fields, e.g. electric, hydrodynamic or centrifugal, and are confronted with challenges that include dispersion-limited resolution, poor sensitivity to low concentrations of oligomers and thermodynamic non-idealities arising from interparticle interactions. Such methods involve complex instrumentation and deliver at best a bulk characterization of the sample.

Recently a method has been commercialized by Nanosight Ltd., Amesbury, Wiltshire, UK (www.nanosight.com), which is termed "Nanoparticle Tracking Analysis" or briefly "NTA". In NTA, Brownian motion of laser-illuminated particles is analyzed in real time by a CCD camera, each particle being simultaneously and separately visualized and tracked by a dedicated computer program. The average distance each particle travels during a certain time period in the absence of any external fields is determined, the diffusion coefficient is derived therefrom, and size is deduced by applying the Stokes-Einstein equation. It has further been suggested to use NTA for measuring the zeta potential of the particles, based on measurements of the velocity of the particles in an applied electric field (electrophoresis). However, the analysis is complicated by the fact that also the fluid moves in response to the applied field (electroosmosis), which needs to be corrected for. The fact that the fluid velocity has a non-trivial spatial dependence introduces further difficulties. The method requires a relatively large field of view of the camera to simultaneously measure the motion of a large number of particles. This can limit the time resolution of imaging and can in turn place limits on the particle velocities which can be measured. Furthermore, the absence of control over the starting configuration of particles under study makes the particle-tracking process prone to further error. Finally, the zeta potential is only a very indirect measure of charge, whereas it is often desired to obtain a more direct measure of the charge of an object.

It has been recently suggested to individually trap charged nanoscale objects suspended in a fluid at high densities in a landscape of electrostatic traps on a chip (Krishnan, M., Mojarad, N., Kukura, P. & Sandoghdar, V.: Geometry-induced electrostatic trapping of nanometric objects in a fluid. Nature 467, 4 (2010), in the following referred to as Ref. [1]). Objects in suspension introduced onto the chip sample the landscape by Brownian (i.e., thermal) motion and fall into local potential wells, remaining trapped in them for a time period that scales as $\exp(\Delta U/k_B T)$, where the electrostatic system free energy U is a function of the spatial location of the object, $k_B T$ is the thermal energy at temperature T, and $k_B$ is the Boltzmann constant. While it has been suggested to utilize such traps for contact-free confinement of single proteins and macromolecules, for the sorting and fractionation of nanometer-sized objects or for their assembly into high-density arrays for photonics applications, the use of such traps for charge or size measurements has not yet been considered.

SUMMARY OF THE INVENTION

It is an object of the present invention to provide a method for obtaining size and/or charge information for single objects in a fluid, which is simple and which can readily be parallelized.

It is another object of the present invention to provide an apparatus specifically adapted to carrying out such a method.

It is yet another object to provide software which causes a computer to carry out the essential analysis steps of the method so as to provide the desired size and/or charge information.

Further embodiments of the invention are laid down in the dependent claims.

The invention provides a method for determining charge and/or size of an object suspended in a fluid, the method comprising:

introducing the object, together with the fluid, into an electrostatic trap defining an electrostatic confining potential;

observing thermal motion of the object in the fluid under influence of the confining potential; and determining at least one of charge and size from the observed thermal motion.

According to the invention, the thermal motion of individual objects in an electrostatic trap is observed. The objects under investigation are preferably nanoscale objects, i.e. objects in a size range of typically 1 to 500 nm, preferably of about 5 to about 100 nm. The objects are suspended in a fluid. The fluid is preferably an aqueous liquid, in particular, an aqueous electrolyte solution, but can be any other liquid which is compatible with the electrostatic trap. Observing thermal motion of an individual trapped object enables a direct measurement of its size and charge, as will be explained further below. In particular, the viscous drag on the object yields a measure of its size, while the stiffness of its confinement can be compared with a potential model to reveal the total charge it carries.

The proposed method enables sample characterization at the single-object level. It is simple, rapid and can be implemented with standard optical imaging instrumentation. Only very small (picoliter) volumes of sample are needed. No electrodes or additional complexity for the application of external fields, e.g., electric fields, is needed.

The proposed method is somewhat reminiscent of Millikan's oil drop experiment (1910) in that the individual motion of a single object is observed under the influence of an electrostatic potential; however, in contrast to the Millikan experiment, the statistical properties of the object's motion rather than its ballistic behavior in an applied electric field are observed, and gravity no longer plays a role. The method may be applied in a variety of different fields, e.g., for highly sensitive detection of molecular binding events or for dynamic single-charge resolved measurements at the solid-liquid interface.

In particular, the method may comprise:
  determining at least one characteristic of the confining potential from the observed thermal motion; and
  comparing the determined characteristic with a potential model to determine at least one of charge and size of the object.

The potential model can be obtained by calculating the system free energy. This calculation can be based on a computational framework like Poisson-Boltzmann theory and can in particular involve numerically solving the Poisson-Boltzmann equation. Alternatively, it is conceivable to model the potential by a molecular-dynamics simulation or by any other suitable method.

The characteristic of the confining potential can be determined from a measurement of at least one characteristic of the probability density distribution of the displacement of the object in the confining potential. In particular, if the complete probability density distribution is at least approximately known from the measurement, the (approximate) confining potential may be determined from the (approximate) probability distribution by applying the Boltzmann relation $U(r)/k_B T = -\ln P(r)$, possibly in an appropriately discretized form.

If the confining potential can be well approximated by a harmonic potential or by another potential shape which can be characterized by a single parameter, it may be sufficient to determine a single parameter of the confining potential as its only relevant characteristic. This parameter will in the following be referred to as a "stiffness parameter". In particular, in the case of a harmonic potential, the stiffness parameter may be the spring constant k of the harmonic potential $U(r) = \frac{1}{2}kr^2$, where r is the distance from the potential minimum along a given direction. In more general terms, the stiffness parameter may be a measure of the second spatial derivative of the confining potential around its minimum.

The object will usually be observed with a camera having a finite exposure time. Determining the "true" probability density distribution P(r) would require measurements at extremely short exposure times, much smaller than the characteristic timescale of particle motion in the potential, e.g., than the relaxation time of the object under investigation. As will be explained in more detail below, a stiffness parameter can however be determined even for relatively long exposure times by applying the following procedure:
  imaging the thermal motion of the object with at least two different exposure times;
  determining, for at least two different exposure times, a width parameter of the apparent probability density distribution;
  deriving a relaxation time of the object from a comparison of the width parameters determined at the different exposure times; and
  calculating the stiffness parameter from the relaxation time.

The width parameter determined at the different exposure times may be, in particular, the measured apparent mean square displacement (MSD) of the object or the variance of the apparent probability density distribution at the given exposure time.

The method can further involve determining a drag parameter, in particular, the so-called drag coefficient γ, where $\gamma = 3\pi\eta\alpha$ for a sphere of diameter α in a fluid of viscosity η. In particular, in case of a harmonic potential, the spring constant (stiffness parameter) k can then be calculated from the relaxation time τ by the formula $k = \gamma/\tau$. Instead of determining the drag coefficient γ, any other parameter which indicates viscous drag, such as the diffusion coefficient, may be determined.

The drag parameter can be determined by an independent measurement, e.g., by observing short-term diffusion behavior (i.e. diffusion behavior on time scales smaller than the relaxation time) of the object, either in the same confining potential or in a different potential such as a square-well potential. It is however also possible to derive both the relaxation time and the drag parameter from a comparison of the width parameters at different exposure times, as will also be explained in more detail below.

Determination of the size of the object can be carried out completely independently of determination of the charge of the object, or it can be carried concomitantly with charge determination. Independent size determination can be achieved, e.g., by determining a drag parameter, as explained above, and calculating the size of the object from the drag parameter, independently of any determination of the characteristics of the potential. The drag parameter can be determined, in particular, by observing the short-term diffusion behavior of the object, as explained above.

The invention further provides an apparatus for determining size and/or charge of an object suspended in a fluid, the apparatus comprising:
  an electrostatic trap for receiving the object together with the fluid and for trapping the object in an electrostatic confining potential;
  an imaging device for observing thermal motion of the object under influence of the confining potential; and
  an analyzing device configured to receive information about the thermal motion from the imaging device and to determine at least one of size and charge of the object from the thermal motion.

The electrostatic trap is preferably constructed as described in the above-identified Reference [1], whose contents are incorporated herein by reference in their entirety for teaching suitable electrostatic traps. In particular, the trap can comprise two substrates arranged in an opposing configuration so as to form a fluidic slit, the substrates having non-zero surface charge densities in the presence of the fluid, inducing an electrostatic potential between the substrates, at least one of the substrates having a surface microstructure or nanostructure (i.e. a structure with at least one lateral dimension below 1 micrometer) for modulating the electrostatic potential between the substrates so as to generate said electrostatic confining potential. At least one of the substrates should be transparent to light to enable observation with the imaging device and can, in particular, consist of glass. As described in Reference [1], the electrostatic traps can be arranged in a one- or two-dimensional array. In this case, a plurality of objects can be observed in parallel in the array of traps, each object being confined in a different trap, and size and/or charge can be determined for each one of the plurality of objects. This enables rapid high-throughput measurements of size and/or charge for a large number of individual particles. However, the invention is in no way limited to any specific type of electrostatic trap and can be employed by using any type of trap which provides a suitable confining potential.

The imaging device can be any suitable microscope capable of determining the object's position with sufficient spatial precision and time resolution. In particular, the imaging device should preferably be capable of achieving a localization accuracy of better than 50 nm, more preferably better than 20 nm, and time resolution better than 1 ms, more preferably better than 500 µs, the exact numbers depending on the type of object under investigation and on trap size. Suitable imaging devices include, e.g., wide-field or scanning confocal fluorescence, dark-field and interferometric scattering microscopy (iSCAT).

The analyzing device of the above-mentioned apparatus can be specifically configured to carry out any of the methods described above. The analyzing device may in particular comprise a computer receiving information from the imaging device and being programmed in such a way that it carries out the necessary steps for determining at least one of size and charge of the object from the received information, as described above. The information received by the analyzing device may, e.g., be image information or preprocessed information derived from image data.

The invention further relates to a computer program product comprising computer program code means for controlling one or more processors of a computer such that the computer carries out the following steps:

receiving information from an imaging device about thermal motion of an object suspended in a fluid under influence of a confining potential in an electrostatic trap; and determining at least one of charge and size of the object from the received information.

In particular, the computer program code means can be specifically configured to control the processor(s) such that the computer carries out any of the specific methods for charge and/or size determination described above.

The computer program product can be provided on a computer-readable medium such as a CD-ROM, DVD-ROM or stored in any other suitable non-volatile memory device, e.g. a flash memory device, or can be provided in non-physical form through a data communication system, e.g., it can be made available for download through a network such as the Internet. The computer program code means can take any suitable form, in particular the form of source code in any suitable programming language, of object code or of machine-executable code.

BRIEF DESCRIPTION OF THE DRAWINGS

Preferred embodiments of the invention are described in the following with reference to the drawings, which are for the purpose of illustrating the present invention and not for the purpose of limiting the same. In the drawings.

DESCRIPTION OF EXEMPLARY EMBODIMENTS

Figure 1:
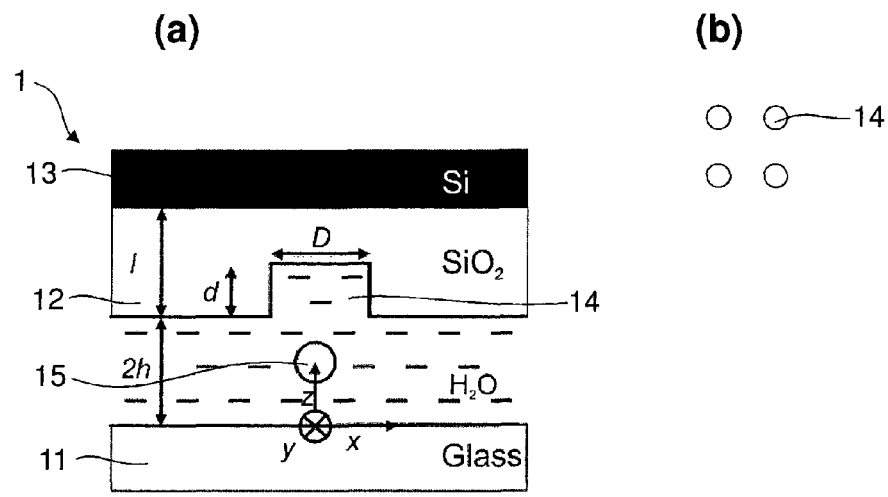
FIG. 1 shows, in cross section, the geometry of a single electrostatic fluidic trap (part (a)) and a possible arrangement of traps into an array (part (b))

FIG. 1(a) illustrates the setup of a single electrostatic trap 1, and FIG. 1(b) illustrates a possible arrangement of traps in an array. An array of such traps was fabricated by lithographically patterning the surface of a ~400 nm deep silicon dioxide layer 12 on a p-type silicon substrate 13 and subsequent wet-etching the silicon dioxide layer 12 to a depth of 2 h≈200 nm in buffered HF (Ammonium fluoride-HF mixture, Sigma-Aldrich). The floors of these trenches were then patterned with submicron-scale features such as cylindrical pockets 14 having a pocket diameter D using electron beam lithography and subsequent reactive ion etching of the silicon dioxide to a pocket depth of d=100 nm. A fluidic device with fully functional fluidic slits having a depth 2 h of approximately 200 nm and a width of 20 micrometers was obtained by irreversibly bonding the processed silicon dioxide-silicon substrates with a glass substrate 11 compatible with high-NA microscopy (PlanOptik, AG) using field-assisted bonding. For details, reference is made to Reference [1], "Methods" section.

Gold nanospheres 15 having a diameter of 80 nm (British Biocell International) were centrifuged and resuspended in deionized $H_2O$ (18 M$\Omega$cm$^{-1}$) twice to remove traces of salt or other contaminants. Nanoslits loaded with an aqueous suspension of the nanometric object of interest (number density ca. $10^{10}$ p/ml for gold particles) by the capillary effect, were allowed to equilibrate at room temperature for 1-2 h before commencing with optical measurements.

Figure 2:
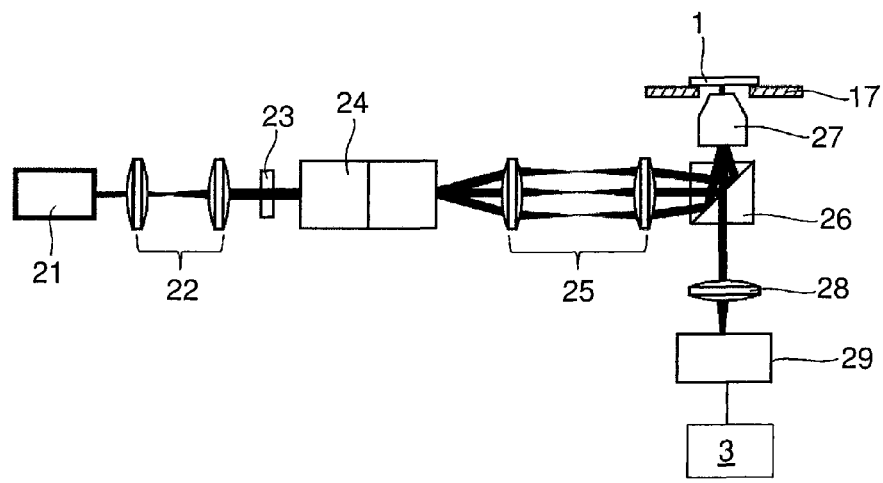
FIG. 2 shows a diagram illustrating the experimental set-up used for iSCAT imaging.

High-speed interferometric scattering detection (iSCAT) was used to image the 3D motion of individual particles trapped in harmonic potential wells created by pockets 14 of diameter D=200 nm or 500 nm and depth d=100 nm in a fluidic slit of depth 2 h=215 nm, using an imaging device 2 in the form of a laser scanning microscope set-up shown in FIG. 2. The gaussian output beam of a 30 mW diode-pumped solid state laser 21 (TECGL-30, WSTech) at $\lambda$=532 nm was expanded by a 4× telescope lens system 22 and passed through a half-wave plate 23 for polarization adjustment, followed by a two-axis acousto-optic deflector (AOD) 24 (DTSXY, AA Opto-Electronic). The deflected beam was delivered via a telecentric system 25 and a beamsplitter cube 26 to the back focal plane of a microscope objective 27 (1.4 NA, 100× UPLASAPO-Olympus) mounted on an inverted microscope equipped with a three-dimensional piezoelectric translation stage 17 (PT1, Thorlabs). The fluidic device comprising the traps 1 was positioned using the translation stage 17 such that the scanned beam illuminated the area of interest. The scanning rates of the AODs were between 50 kHz and 100 kHz and were adjusted to achieve a uniform wide field of illumination for a given exposure time. Light scattered by the particle and reflected by the device was collected by the same microscope objective 27 and imaged via a tube lens 28 onto a CMOS camera 29 (MV-D1024E-160-CL-12, Photonfocus). Image data from the camera 29 was transferred to an analyzing device 3 in the form of an appropriately programmed general-purpose computer, which carried out the subsequent analysis of the image data as described in more detail below.

When imaging a trapped particle using interferometric scattering detection (iSCAT), the detected signal results from the interference of the electromagnetic field scattered by the particle, the background pocket, and the beam reflected from the $SiO_2$/Si interface. The interference allows determining complete information on the 3D location of the particle, not only along the lateral plane, but also along the axial direction. For details, reference is made to Reference [1], "method" section (see above). The gold nanospheres gave a signal-to-noise ratio (SNR) of ~100 suitable for particle tracking with a localization precision of ~2 nm. They also carried a substantial amount of charge, of the order of −100 e, making them amenable to trapping for long periods of time (several minutes to hours) and therefore convenient to study.

Figure 3:
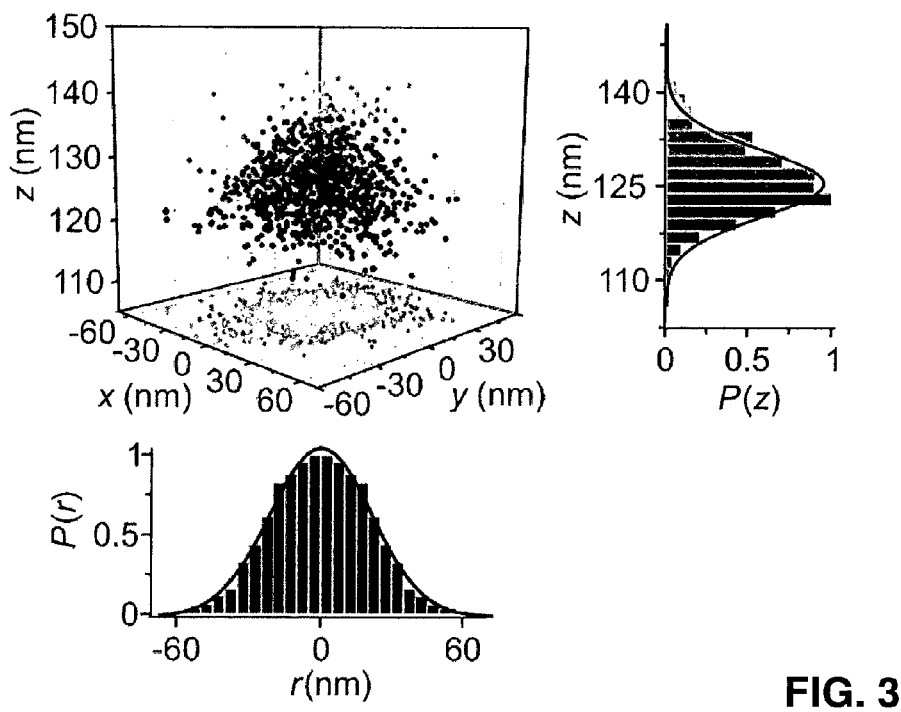
FIG. 3 shows a 3D scatter plot of positions x, y, z for a representative particle and corresponding histograms for the probability distributions P(r) and P(z) of position in radial coordinate r and axial coordinate z, respectively.
Figure 4:
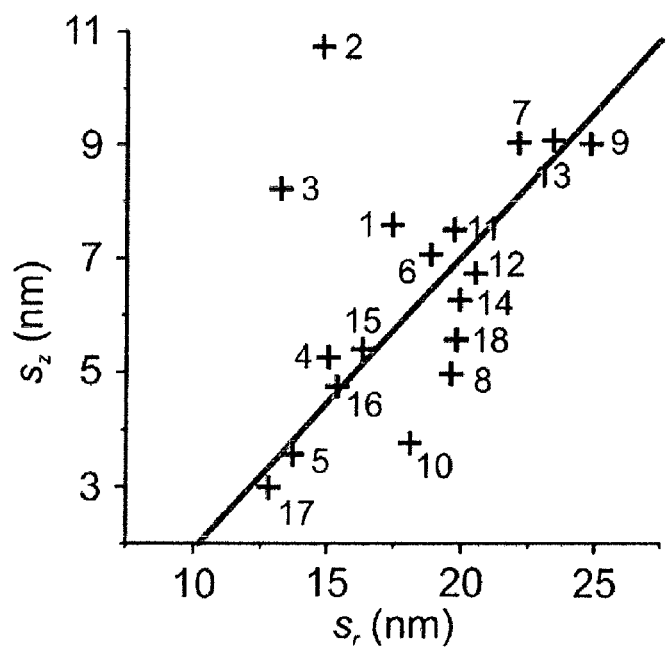
FIG. 4 shows a plot of the r.m.s. values of axial displacement $s_z$ vs. lateral displacement $s_r$ for 18 different particles, numerals adjacent to each data symbol representing particle serial number.

The observed 3D motion of single trapped particles is presented in FIGS. 3 and 4. As apparent from FIG. 3, the particles sample the confining potential both in the radial (lateral) direction and in the axial direction with a near-Gaussian probability distribution. The spatial sampling of an electrostatic potential well by a particle strongly depends on the charge it carries: the higher the charge on the particle, the greater the expected stiffness of its confinement, which manifests in the experiment as a smaller r.m.s. spatial displacement. Importantly, any increase or decrease in stiffness arising from particle charge would be expected to appear in all spatial dimensions. A scatter plot of the r.m.s. displacement of each particle in the axial ($s_z$) vs. radial dimension ($s_r$) is shown in FIG. 3. This plot convincingly demonstrates just this correlation. The fact that $s_z < s_r$ confirms higher trap stiffness in the axial compared to the radial dimension. The solution ionic strength in these measurements was 0.04 mM. Measuring the trap stiffness thus presents a simple and rapid route to measure the relative charge dispersion in a sample at the single object level.

In order to measure the absolute net charge carried by any given particle, the characteristics of the confining potential, as determined by the measurements, can be compared with a potential model obtained from numerical calculations. In particular, if the probability density distribution of particle displacement P(r) has been measured, the Boltzmann relation, $U(r)/k_BT = -\ln P(r)$, yields the spatially dependent potential U(r). Once this potential is known, the charge of the particle can be directly obtained by comparison with a model obtained from free energy calculations.

Figure 5:
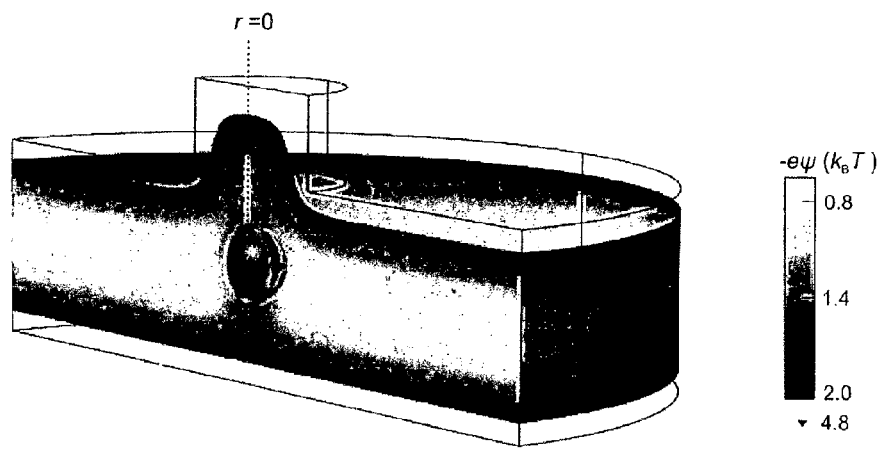
FIG. 5 shows a diagram illustrating the calculated distribution of electrostatic potential ψ in a three-dimensional cylindrical half-space around a particle 80 nm in diameter in a trapping nanostructure with D=200 nm and 2 h=215 nm, the displayed range being truncated at a potential $e\psi = -2 k_B T$.

COMSOL Multiphysics was used to create such a potential model by calculating the spatial distribution of electrostatic potential in the trapping nanostructure by numerically solving the non-linear Poisson-Boltzmann equation in 3D. As shown in FIG. 5, the model system consisted of a sphere of a fixed surface charge density embedded in an electrolyte, which in turn is bounded by surfaces of a given charged density representing the walls of the trapping nanostructure. The inputs to the calculation were the wall charge density, the solution ionic strength and the size and surface charge density of the object. The background electrolyte ionic strength and an estimate of the wall charge density were obtained from conductivity and electroosmotic flow measurements, respectively. Thus, for a particle of a given diameter, its charge remained the only free parameter in the calculation. The free energy of the system as a function of particle position was calculated by summing the electrostatic field energies and entropies over all charges in the system.

Figure 6:
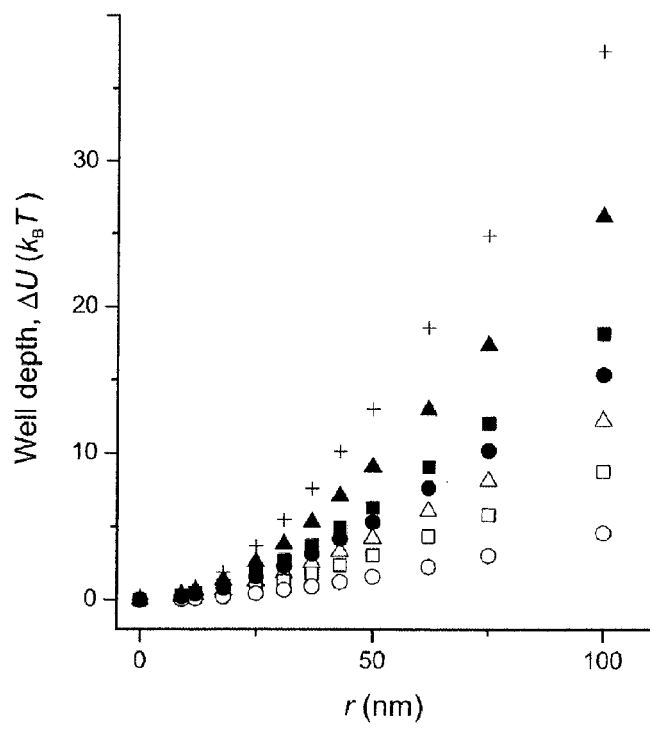
FIG. 6 shows radial free energy profiles calculated along the contour of the axial energy minimum for particle charges q=−40 (open circles), −88 (open squares), −133 (open triangles), −177 (solid circles), −221 (solid squares), −398 (solid triangles) and −1105 e (crosses), for a solution ionic strength 0.04 mM.
Figure 7:
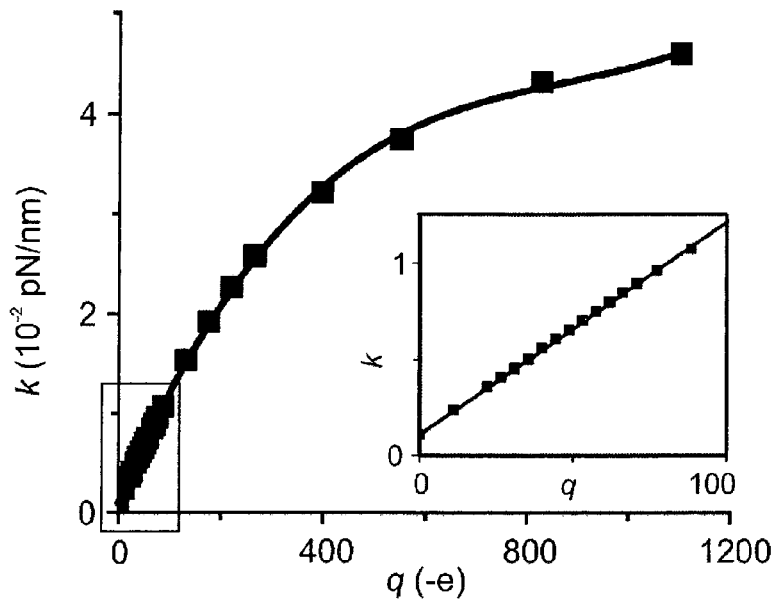
FIG. 7 shows a diagram illustrating the variation of the spring constant of confinement k with particle charge q, the inset displaying a linear relationship between k and q for q<−100 e (black line)
Figure 8:
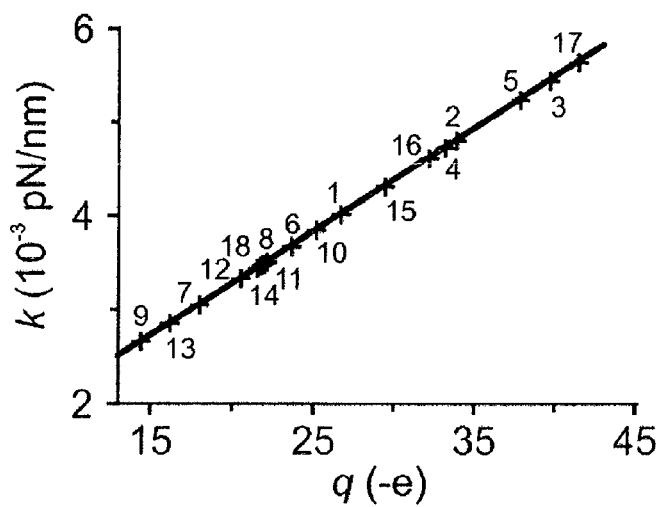
FIG. 8 shows a diagram illustrating the charge deduced for each particle in FIG. 4 (symbols) based on the k vs. q relationship in FIG. 7 (solid line)

FIG. 6 shows a series of calculated radial free energy curves as a function of particle charge q for the conditions of the measurements in FIGS. 1-4. The free energy curves were fitted to a function $U(r) = \frac{1}{2}kr^2$ for r<50 nm to obtain the spring constant of confinement k in each case. The relationship between k and q derived from such comparisons is shown in FIG. 7. This figure enables a direct readout of the charge of a particle once its spring constant is known. Further, the linearity of the relation for q<−100 e and the low uncertainty in the single fit coefficient (~0.5%) implies that if the particle's spring constant is measured with a comparable accuracy, the measurements could be very close to single-charge resolved (FIG. 7 inset). This raises prospects both for fundamental studies on (dis-) charging processes on matter in solution as well as for ultrasensitive single-nanoparticle based molecular binding sensors.

The procedure outlined above requires that snapshots of the particle can be acquired with a high signal-to-noise ratio and at exposure times which are much shorter than the relaxation times of the particles. Provided that these conditions are fulfilled, optical imaging is an excellent calibration-free method for direct mapping of potential landscapes of arbitrary shape and large range, and offers distinct advantages in high-throughput analysis of a dense array of trapped objects.

Unfortunately, high SNR imaging with an exposure time much smaller than the relaxation time of the particle can be challenging. In a harmonic confining potential, however, the spring constant of confinement k can be obtained even for exposure times which are comparable or even larger than the relaxation time τ of the particle. This will explained in the following.

The spring constant and the relaxation time are related via the drag coefficient γ as k=γ/τ (Equation 1), where γ=3πηa for a sphere of diameter a in a solution of viscosity η. A spring constant of k=7.5×10⁻³ pN/nm for example, easily achieved for the particles under consideration, corresponds to a relaxation time of around 100 μs, assuming η=1×10⁻³ kg/ms, the viscosity of water in free solution. If the drag coefficient is known, a measurement of the relaxation time thus yields the spring constant.

The motion of a single particle can be investigated using different exposure times, σ>τ and the corresponding apparent mean squared displacements (MSD) $\langle [\Delta x(t, \sigma)]^2 \rangle$ can be evaluated as a function of lag time t. Rather than continuously increasing as a function of t, the MSD of a trapped particle eventually saturates at a value $$\langle [\Delta x]_p^2 \rangle = \frac{2k_B T}{k}$$

for a harmonic trapping potential. In this case, the plateau value of the MSD, $\langle [\Delta x(\sigma)]_p^2 \rangle$ measured using an exposure time, σ approaches the true value asymptotically as a function of the σ/τ ratio:

$$\frac{\langle [\Delta x(\sigma)]_p^2 \rangle}{\langle [\Delta x]_p^2 \rangle} = \frac{2}{\sigma/\tau} - \frac{2(1 - e^{-\sigma/\tau})}{(\sigma/\tau)^2}. \quad \text{(Equation 2)}$$

Figure 10:
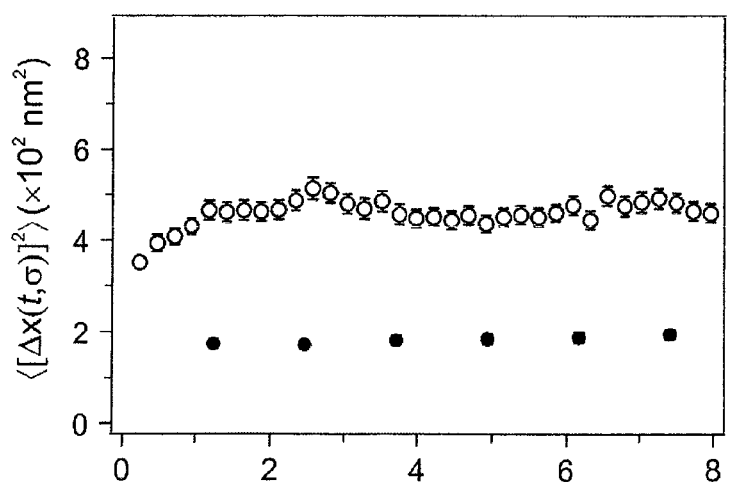
FIG. 10 shows a diagram illustrating apparent MSD in x for a particle trapped by a D=200 nm pocket and imaged using exposure times σ=0.2 ms (open circles) and 1 ms (solid circles)

This is illustrated in FIG. 10 for a selected particle trapped in a 200 nm pocket, imaged at exposure times of 0.2 ms and 1 ms, respectively. Using the values of $\langle [\Delta x(\sigma)]_p^2 \rangle$ from the MSD measurements, Equation 2 gives the relaxation time and, through Equation 1, the spring constant of confinement for the particle under consideration. A relaxation time of τ=85±5 μs was obtained for the selected particle.

Figure 11:
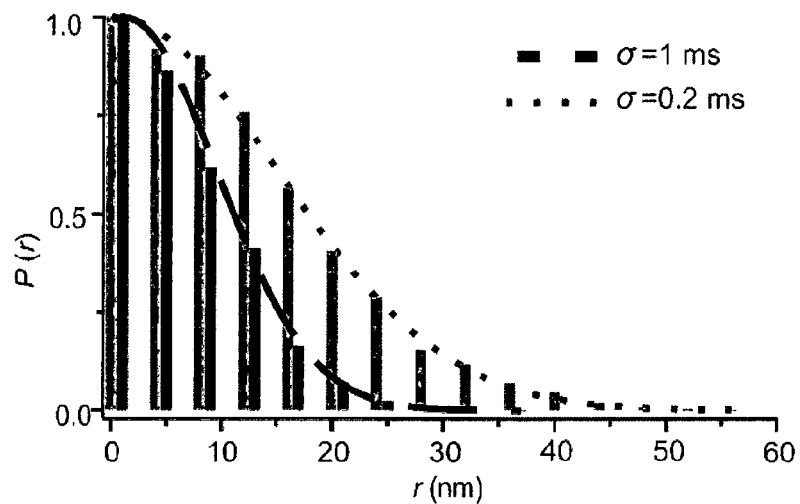
FIG. 11 shows radial probability histograms P(r) corresponding to the apparent MSD data of FIG. 10 for exposure times σ=0.2 ms (grey bars, dotted line) and 1 ms (black bars, dashed line)

Note that the same result may be obtained from an analysis which uses the apparent variance $s_x^2$ of the measured probability distribution P(x) in x (or y), as shown in FIG. 11, in place of $\langle [\Delta x(\sigma)]_p^2 \rangle$, and which uses the true variance $$\frac{k_B T}{k}$$

in place of $\langle [\Delta x]_p^2 \rangle$.

Figure 12:
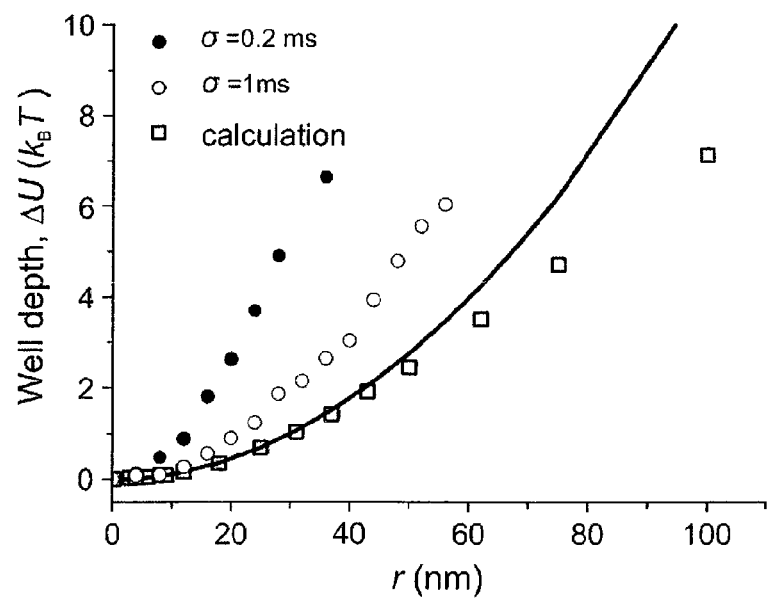
FIG. 12 shows a diagram illustrating the apparent local electrostatic potential U(r) derived from the P(r) data shown in FIG. 12 for σ=0.2 ms (solid circles) and 1 ms (open circles), together with a solid curve representing a harmonic potential of the form $U(r) = \frac{1}{2}kr^2$ with $k=8.8 \times 10^{-3}$ pN/nm inferred from the experimental MSD data, square symbols representing the calculated free energy for a particle of charge −62 e.
Figure 13:
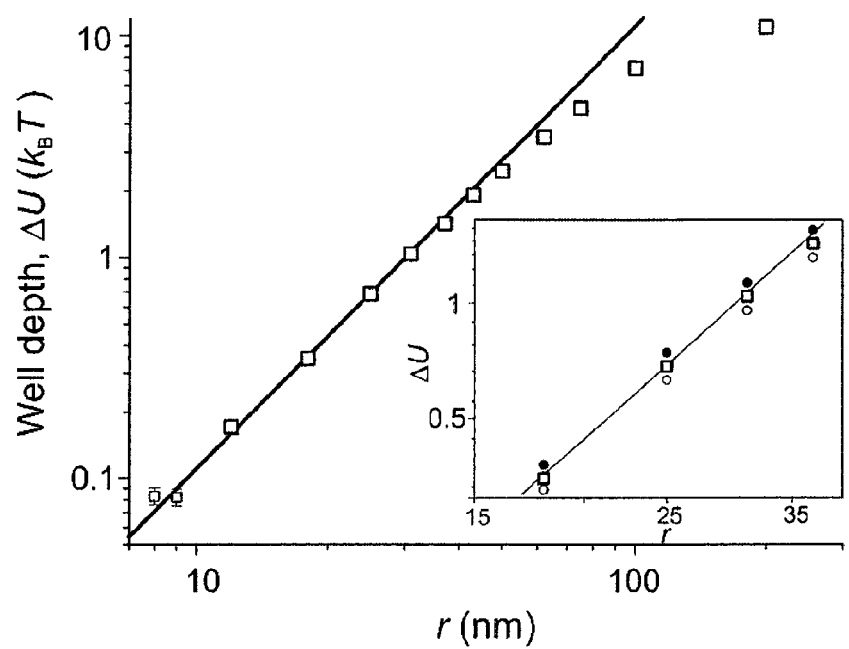
FIG. 13 shows a log-log plot of the experimentally inferred potential and calculated free energy shown in FIG. 12, the inset presenting a zoomed view of the experimental potential (solid line) and free energy calculations (symbols) for particles of charge q=−54 e (open circles), −62 e (open squares), and −68 e (solid circles).

A value of τ=85 μs corresponds to a spring constant of confinement k=8.8×10⁻³ pN/nm, depicted by the lines in FIGS. 12 and 13. A similar analysis can be carried out for other potential shapes.

Having experimentally deduced the true spring constant of confinement, the measurement can be compared with the calculation to obtain the charge of the particle. The squares in FIGS. 12 and 13 represent the free energy as a function of radial distance from the trap center r calculated for a particle 80 nm in diameter carrying a total surface charge of −62 e; the wall charge density and background electrolyte concentration were −0.01 e/nm² and 0.03 mM respectively. The uncertainty in the measured relaxation time implies that the charge on a single particle can be determined to within ±10% (FIG. 13 inset). The precision in the relaxation time can be enhanced with measurements at additional exposure times, albeit at the possible expense of time resolution in the overall charge measurement. Further, the charge on the particle deduced from its lateral motion can be independently confirmed by a similar analysis of its motion in the axial dimension.

Experimental relaxation times and deduced net charges for four different particles are presented in the following table. The solution ionic strength for particles (i-iii) was 0.03 mM, while that for particle (iv) was 0.04 mM.

| particle | τ (μs)   | q (e)     |
|----------|----------|-----------|
| i        | 85 ± 5   | −54−−68   |
| ii       | 87 ± 13  | −49−−75   |
| iii      | 85 ± 4   | −54−−68   |
| iv       | 161 ± 11 | −26−−35   |

Figure 9:
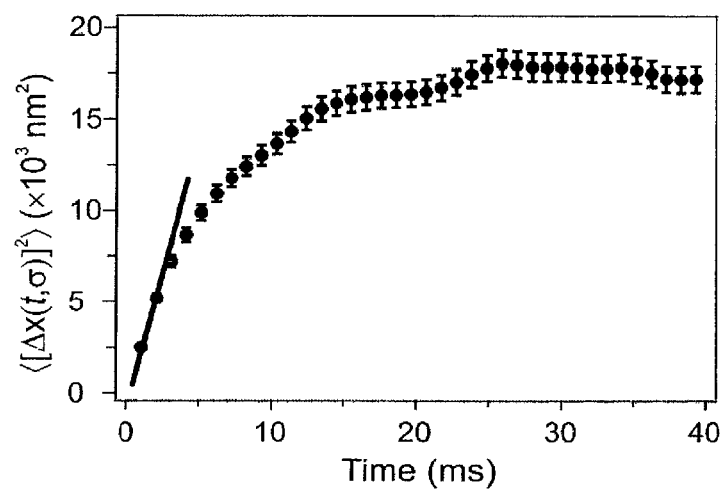
FIG. 9 shows a diagram illustrating the apparent mean square displacement (MSD) in x, $\langle [\Delta x(t, \sigma)]^2 \rangle$, as a function of lag-time t for a particle trapped by a D=500 nm pocket imaged with an exposure time σ=1 ms, together with a linear fit to the data for t<3 ms.

The size of the particles can be measured independently. One way to do this is via an analysis of the MSD of the trapped particle. The data series in FIG. 9 shows MSD data for a particle trapped in a well created by a D=500 nm pocket, which may be roughly approximated by a square well. Fitting the linear portion of the data, a translational diffusion coefficient of 1.62±0.17 μm²/s was obtained, averaged over 10 different cases. The measured diffusivity, $$\frac{k_B T}{\gamma}$$

of the particle yields its hydrodynamic diameter which can then serve as an input to the free energy calculation. An alternative route is to leave the quantity $$\langle [\Delta x]_p^2 \rangle = \frac{2k_B T}{\gamma} \tau$$

in Eq. 2 as a free parameter and obtain both γ and τ from the fit to measurements at multiple exposure times.

Interestingly, the free energy calculations suggest that for a given particle charge, the size of the particle starts to contribute more strongly to the shape of the trap at longer range, say r>80 nm, than it does closer to the center (r<50 nm). An accurate long-range spatial map of the potential could therefore further provide an independent measurement of the particle diameter.

The present invention thus shows that a few seconds worth of high spatio-temporal resolution imaging of electrostatically trapped objects can yield both size and charge information on thousands of individual entities trapped in parallel in high-density arrays. This equilibrium measurement directly addresses the surface of a single nano-object, raising prospects for measuring charge fluctuations in matter, monitoring the progress of chemical reactions in real time and fostering the elucidation of fundamental phenomena at the poorly understood solid-liquid interface.

The method may be extended to higher solution ionic strengths by employing smaller slit depths $$\left(h \sim \frac{1}{\sqrt{C}}\right)$$

for effective trapping.

Although iSCAT was used in the above example, a variety of other imaging techniques that deliver sufficient spatial and temporal resolution, e.g. wide-field or laser scanning fluorescence, or dark field microscopy may be used to the same end. Given further advances in high-speed, high-sensitivity imaging technology, weakly scattering but labeled entities that are only transiently trapped (<1 s)—such as small and/or weakly charged matter, or biological macromolecules in solutions of higher ionic strength—could be studied by this technique. Progress in imaging based on scattering or absorption would go a long way in fostering label-free measurements of this nature on nanoscopic entities.

It goes without saying that the present invention is not limited to the above-described example. In particular, differently shaped traps may be employed, depending on the nature of the objects under investigation. For example, the traps may be elongated for elongated objects such as nanofibers. While in the above-described example electrostatic traps were obtained by surface patterning in a fluid slit according to Ref. [1], other types of electrostatic traps may be employed.

The invention claimed is:

1. A method for determining at least one of charge and size of an object suspended in a fluid, the method comprising:
introducing the object, together with the fluid, into an electrostatic trap defining an electrostatic confining potential (ΔU);
with an imaging device, observing thermal motion of the object in the fluid under influence of the confining potential (ΔU); and
with an analyzing device connected to the imaging device, determining at least one of charge and size from the observed thermal motion, wherein at least one characteristic of the confining potential is determined by the analyzing device from the observed thermal motion and is compared with a potential model of the confining potential, thereby determining at least one of charge and size of the object.

2. The method of claim 1, wherein the characteristic of the confining potential (ΔU) is determined by measuring at least one characteristic of a probability density distribution (P(r)) of object displacement under influence of the confining potential and deriving the characteristic of the confining potential from said characteristic of the probability density distribution (P(r)).

3. The method of claim 2, wherein determining the stiffness parameter comprises: with the imaging device connected to the analyzing device, imaging the thermal motion of the object with at least two different exposure times (σ);
determining, for the at least two different exposure times (σ), a width parameter of the apparent probability density distribution;
deriving a relaxation time (τ) of the object from a comparison of the width parameters at the different exposure times (σ); and
calculating the stiffness parameter (k) from the relaxation time (τ).

4. The method of claim 3, wherein the drag parameter (γ) is determined from an observation of short-term diffusion behavior of the object.

5. The method of claim 1, wherein the characteristic of the confining potential is a stiffness parameter (k) of the confining potential (ΔU).

6. The method of claim 5, further comprising:
with the imaging device and the analyzing device connected to the imaging device, determining a drag parameter (γ) for the object,
wherein the stiffness parameter (k) is calculated from the relaxation time (τ) using the drag parameter (γ).

7. The method of claim 5, wherein both the relaxation time (τ) and a drag parameter (γ) are derived by the analyzing device from a comparison of the width parameters at the different exposure times (σ).

8. The method of claim 1, further comprising: obtaining with the analyzing device, the potential model by carrying out a calculation of system free energy.

9. The method of claim 1, comprising: with the imaging device and the analyzing device connected to the imaging device, determining a drag parameter (γ) of the object within the confining potential; and calculating the size of the object from the drag parameter (γ).

10. The method of claim 1, wherein the electrostatic trap comprises two substrates arranged in an opposing configuration so as to form a fluidic slit, the substrates having non-zero surface charge densities inducing an electrostatic potential between the substrates, at least one of the substrates having a surface nanostructure for modulating the electrostatic potential between the substrates so as to generate said electrostatic confining potential.

11. The method of claim 1, wherein a plurality of objects are observed by the imaging device in parallel in an array of traps, and wherein at least one of size and charge is determined for each one of said plurality of objects.

12. An apparatus for determining at least one of size and charge of an object suspended in a fluid, the apparatus comprising:
an electrostatic trap for receiving the object together with the fluid and for trapping the object in an electrostatic confining potential;
an imaging device for observing thermal motion of the object under influence of the confining potential; and
an analyzing device connected to the imaging device, and configured to receive information about the thermal motion from the imaging device and to determine at least one of size and charge of the object from the observed thermal motion,
wherein the analyzing device is configured to determine at least one characteristic of the confining potential (ΔU) from the observed thermal motion and to compare the determined characteristic with a potential model to determine at least one of charge and size of the object.

13. The apparatus of claim 12, comprising an array of electrostatic traps for receiving a plurality of objects in parallel, wherein the analyzing device is configured to determine at least one of size and charge of each one of the plurality of objects .

14. The apparatus of claims 12, wherein the electrostatic trap comprises two substrates arranged in an opposing configuration so as to form a fluidic slit, the substrates having non-zero surface charge densities inducing an electrostatic potential between the substrates, at least one of the substrates having a surface nanostructure for modulating the electrostatic potential between the substrates so as to generate said electrostatic confining potential.

15. An analyzing device configured to execute the steps of a computer program code, the steps of the computer program code comprising: receiving information from an imaging device about thermal motion of an object suspended in a fluid under influence of a confining potential in an electrostatic trap ; and determining at least one of charge and size of the object from the received information, by determining at least one characteristic of the confining potential ($\Delta U$) from the received information; and comparing the determined characteristic with a model potential to determine at least one of the charge and size of the object.

* * * * *